United States Patent
Kitching et al.

(10) Patent No.: US 10,624,716 B2
(45) Date of Patent: *Apr. 21, 2020

(54) SYSTEM AND METHOD FOR DETECTING DEVIATIONS DURING THE COURSE OF AN ORTHODONTIC TREATMENT TO GRADUALLY REPOSITION TEETH

(71) Applicant: Align Technology, Inc., San Jose, CA (US)

(72) Inventors: Ian Kitching, Saratoga, CA (US); Ka M. Cheang, Sunnyvale, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 365 days.

This patent is subject to a terminal disclaimer.

(21) Appl. No.: 14/952,642

(22) Filed: Nov. 25, 2015

(65) Prior Publication Data

US 2016/0074138 A1 Mar. 17, 2016

Related U.S. Application Data

(60) Division of application No. 14/152,776, filed on Jan. 10, 2014, now Pat. No. 9,364,297, which is a
(Continued)

(51) Int. Cl.
*A61C 7/08* (2006.01)
*A61C 7/00* (2006.01)
(Continued)

(52) U.S. Cl.
CPC ............... *A61C 7/002* (2013.01); *A61C 7/00* (2013.01); *G06F 19/00* (2013.01); *G16H 50/50* (2018.01)

(58) Field of Classification Search
CPC ................................. A61C 7/002; A61C 7/08
See application file for complete search history.

(56) References Cited

U.S. PATENT DOCUMENTS

| 2,467,432 A | 4/1949 | Kesling |
| 3,407,500 A | 10/1968 | Kesling |
(Continued)

FOREIGN PATENT DOCUMENTS

| AU | 3031677 A | 5/1979 |
| AU | 517102 B2 | 7/1981 |
(Continued)

OTHER PUBLICATIONS

AADR. American Association for Dental Research, Summary of Activities, Mar. 20-23, 1980, Los ngeles, CA, p. 195.
(Continued)

*Primary Examiner* — Ralph A Lewis
(74) *Attorney, Agent, or Firm* — Wilson Sonsini Goodrich & Rosati

(57) ABSTRACT

Method and system for detecting and correcting deviation during an orthodontic treatment plan is provided. The method includes the steps of receiving an un-segmented current teeth image representing a patient's teeth after an orthodontic treatment plan has begun and before the plan ends for the patient; matching a previously segmented teeth model with the current teeth image; and generating at least one corrective stage to define an intermediate tooth arrangement, wherein the at least one corrective stage repositions a digital teeth image so that a prescribed tooth arrangement of the previously segmented teeth model can be used.

29 Claims, 12 Drawing Sheets

Related U.S. Application Data continuation of application No. 13/293,916, filed on Nov. 10, 2011, now Pat. No. 8,636,510, which is a continuation of application No. 11/760,612, filed on Jun. 8, 2007, now Pat. No. 8,075,306.

(51) Int. Cl.
*G16H 50/50* (2018.01)
*G06F 19/00* (2018.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,752,832 A | 5/1998 | Vardimon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,067,523 A | 5/2000 | Bair et al. |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |

(56) References Cited

U.S. PATENT DOCUMENTS

| | | |
|---|---|---|
| 6,398,548 B1 | 6/2002 | Muhammad et al. |
| 6,402,707 B1 | 6/2002 | Ernst |
| 6,406,292 B1 | 6/2002 | Chishti et al. |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,074,038 B1 | 7/2006 | Miller |
| 7,077,647 B2 | 7/2006 | Choi et al. |
| 7,156,661 B2 | 1/2007 | Choi et al. |
| 7,357,636 B2 | 4/2008 | Hedge et al. |
| 7,474,307 B2 | 1/2009 | Chishti et al. |
| 8,075,306 B2 * | 12/2011 | Kitching .................. A61C 7/00 382/128 |
| 8,562,338 B2 | 10/2013 | Kitching et al. |
| 8,636,510 B2 * | 1/2014 | Kitching .................. A61C 7/00 382/128 |
| 8,899,978 B2 | 12/2014 | Kitching et al. |
| 9,017,072 B2 | 4/2015 | Kitching et al. |
| 9,060,829 B2 | 6/2015 | Sterental et al. |
| 9,364,297 B2 * | 6/2016 | Kitching .................. A61C 7/00 |
| 1,005,217 A1 | 8/2018 | Kitching et al. |
| 2001/0002310 A1 | 5/2001 | Chishti et al. |
| 2002/0006597 A1 | 1/2002 | Andreiko et al. |
| 2002/0010568 A1 | 1/2002 | Rubbert et al. |
| 2002/0064746 A1 | 5/2002 | Muhammad et al. |
| 2002/0072027 A1 | 6/2002 | Chishti |
| 2003/0009252 A1 | 1/2003 | Pavlovskaia et al. |
| 2003/0049584 A1 | 3/2003 | Chishti et al. |
| 2003/0139834 A1 | 7/2003 | Nikolskiy et al. |
| 2003/0143509 A1 | 7/2003 | Kopelman et al. |
| 2003/0190575 A1 | 10/2003 | Hilliard |
| 2003/0224311 A1 | 12/2003 | Cronauer |
| 2004/0072120 A1 | 4/2004 | Lauren |
| 2004/0128010 A1 | 7/2004 | Pavlovskaia et al. |
| 2004/0197727 A1 * | 10/2004 | Sachdeva .................. A61C 7/00 433/24 |
| 2004/0202983 A1 | 10/2004 | Tricca et al. |
| 2005/0038669 A1 | 2/2005 | Sachdeva et al. |
| 2005/0048432 A1 | 3/2005 | Choi et al. |
| 2005/0055118 A1 | 3/2005 | Nikolskiy et al. |
| 2005/0089822 A1 | 4/2005 | Geng et al. |
| 2005/0192835 A1 | 9/2005 | Kuo et al. |
| 2005/0241646 A1 | 11/2005 | Sotos et al. |
| 2005/0271996 A1 | 12/2005 | Sporbert et al. |
| 2006/0004609 A1 | 1/2006 | Kenneth et al. |
| 2006/0079981 A1 * | 4/2006 | Rubbert .................. A61C 7/00 700/98 |
| 2006/0121408 A1 | 6/2006 | Hedge et al. |
| 2006/0127836 A1 | 6/2006 | Wen |
| 2006/0147872 A1 | 7/2006 | Andreiko |
| 2006/0194163 A1 | 8/2006 | Tricca et al. |
| 2006/0199142 A1 | 9/2006 | Liu et al. |
| 2006/0263739 A1 | 11/2006 | Sporbert et al. |
| 2006/0286501 A1 | 12/2006 | Chishti |
| 2007/0003900 A1 | 1/2007 | Miller |
| 2007/0072144 A1 | 3/2007 | Imgrund et al. |
| 2007/0099147 A1 | 5/2007 | Sachdeva et al. |
| 2007/0184398 A1 | 8/2007 | Cronauer |
| 2007/0226005 A1 | 9/2007 | Smith et al. |
| 2008/0050692 A1 | 2/2008 | Hilliard |
| 2008/0305451 A1 | 12/2008 | Kitching et al. |
| 2008/0305452 A1 | 12/2008 | Sterental et al. |
| 2008/0305453 A1 | 12/2008 | Kitching et al. |
| 2008/0305454 A1 | 12/2008 | Kitching et al. |
| 2008/0306724 A1 | 12/2008 | Kitching et al. |
| 2012/0225401 A1 | 9/2012 | Kitching et al. |
| 2014/0023980 A1 | 1/2014 | Kitching et al. |
| 2014/0193765 A1 | 7/2014 | Kitching et al. |
| 2014/0335466 A1 | 11/2014 | Kitching et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 1550777 A | 8/1979 |
| GB | 15500777 | 8/1979 |
| JP | 53-058191 | 5/1978 |
| JP | 04-028359 | 1/1992 |
| JP | 08-508174 | 9/1996 |
| JP | H08508174 A | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 2006/065955 * | 6/2006 |
| WO | WO 2006/118771 A2 | 11/2006 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty, NATO Symposium on Applications of Human Biostereometrics," Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

(56) References Cited

OTHER PUBLICATIONS

Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-ALLDENT Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et al. "Computer-Based Image Analysis of Artificial Root Surface Caries, Abstracts of Papers," J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa...>.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).

(56) References Cited

OTHER PUBLICATIONS

Important Tip About Wearing the Red White & Blue Active Clear Retainer System, Allesee Orthodontic Appliances—Pro Lab, 1 page 1998).
JCO Interviews, Craig Andreiko, DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984). Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "PROCERA Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab

(56) References Cited

OTHER PUBLICATIONS product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smiler! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050342, filed Jun. 20,1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthopm vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
Andrews, The Six Keys to Optimal Occlusion Straight Wire, Chapter 3, pp. 13-24 (1989).
Biostar Opeation & Training Manual. Great Lakes Orthodontics, Ltd. 199 Fire Tower Drive, Tonawanda, New York. 14150-5890, 20 pages total (1990).
Dentrac Corporation, Dentrac document, pp. 4-13 (1992).
DuraClearTM product information, Allesee Orthodontic Appliances-Pro Lab, 1 page (1997).
European search report with written opinion dated Mar. 7, 2017 for EP16197945.5.
Rekow et al., "CAD/CAM for Dental Restorations—Some of the Curious Challenges," IEEE Trans. Biomed. Eng., 38(4):314-318 (Apr. 1991).
Richmond, et al. A 2-Center Comparison of Orthodontist's Perceptions of Orthodontic Treatment Difficulty. Jan. 2001, Angle Orthodontist, vol. 71, No. 5, pp. 404-410.
Siemens, "CEREC—Computer-Reconstruction," High Tech in der Zahnmedizin, 14 pages total (2004).
Tru-Tain Orthodontic & Dental Supplies, Product Brochure, Rochester, Minnesota 55902, 16 pages total (1996).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
You May Be a Candidate for This Invisible No-Braces Treatment, Allesee Orthodontic Appliances—Pro Lab product information for patients, 2 pages (2002).

\* cited by examiner

Matching Assistant

The following are teeth that have not been matched:

| Tooth ID | Distance... | Match Status |
|---|---|---|
| 4 | 0.0694 | Inspect for mis-match collision |
| 6 | 0.0960 | fluctuation |
| 7 | 0.0831 | fluctuation |
| 17 | 0.0738 | fluctuation |
| 19 | 0.0676 | inspect for mis-match collision |
| 20 | 0.0739 | fluctuation |
| 25 | 0.0655 | inspect for mis-match collision |
| 32 | 0.0728 | fluctuation |

Advance Properties

Tooth 4-6: Collision statistics mismatch. Was 0.2969mm (now 0.0906mm). Please inspect matching tooth against the impression to make sure that matching is correct.

Average matching distance  0.0694 ___ mm

Please Lower starting distance to be within 0.30mm.

☐ Trim colliding teeth automatically?

[ Re-match ] [ Done ]

FIG. 11

Question

⚠ The following teeth are over the acceptable matching surface limit (0.1000mm)! ([0.1500mm] for last Molar)
  Tooth 23  0.1501
  Tooth 24  0.1557
  Tooth 25  0.1318
  Tooth 26  0.1346

Please go back and rematch them! Teeth not match within limit might create unfitted Aligners. Click YES to go back and rematch.

[ Yes ]   [ No ]—86

FIG. 15

SYSTEM AND METHOD FOR DETECTING DEVIATIONS DURING THE COURSE OF AN ORTHODONTIC TREATMENT TO GRADUALLY REPOSITION TEETH

CROSS-REFERENCE

This application is a divisional of U.S. application Ser. No. 14/152,776, filed Jan. 10, 2014, now U.S. Pat. No. 9,364,297, issued Jun. 14, 2016, which is a continuation of U.S. application Ser. No. 13/293,916, filed Nov. 10, 2011, now U.S. Pat. No. 8,636,510, issued Jan. 28, 2014, which is a continuation of U.S. application Ser. No. 11/760,612, filed Jun. 8, 2007, now U.S. Pat. No. 8,075,306, issued Dec. 13, 2011, the contents of which are hereby incorporated by reference in their entirety.

FIELD OF THE INVENTION

This invention relates to the field of orthodontics, and more particularly to a system and method for detecting deviations from a planned course of treatment to gradually reposition teeth.

BACKGROUND OF THE INVENTION

A fundamental objective in orthodontics is to realign or reposition a patient's teeth to positions where the teeth function optimally and aesthetically. Methods have been developed to reposition a patient's teeth to a prescribed tooth arrangement (i.e. a desired final arrangement of each tooth in a patient's jaw) according to a planned course of treatment using a series of appliances. The series of incremental position adjustment appliances are placed over the patient's teeth and gradually reposition the teeth. Each appliance represents a pre-existing stage in a series of pre-existing stages for repositioning teeth to a prescribed final position. This is described in U.S. Pat. No. 5,975,893; which is assigned to the assignee of the present application, and the complete disclosures of which is incorporated herein by reference.

Ideally, a patient wears each appliance for about two weeks or until the pressure of each appliance on the teeth can no longer be felt. At that point, the patient replaces a current adjustment appliance with a next adjustment appliance in the series until no more appliances remain. During treatment, a patient may forget to wear the appliances regularly allowing the patient to stray from the prescribed course. As a result, one or more appliances may not properly fit and the dentist (or any other medical professional) may have to start the process again ("re-start") by taking another impression of the patient's teeth so that a new series of incremental position adjustment appliances can be electronically generated and ultimately manufactured to a new prescribed tooth arrangement.

When a re-start occurs, there is an opportunity to track what progress has occurred to straighten the patient's teeth. To accurately track the progress of a patient's teeth, it is desirable to have an exact model of the patient's teeth for comparison.

Conventional methods provide process steps for creating generalized record keeping for images of a patient's teeth by moving standard teeth in a standard three-dimensional (3D) digital model template to reflect the general position of a patient's teeth. Since the size and shape of any tooth of the standard 3D model may vary from actual teeth of the patient, the images may only provide a visual likeness and not an exact tooth structure or position to allow for accurate tracking of tooth movement or fabrication of adjustment appliances, such as aligners, which use actual teeth geometry.

In conventional methods, a patient's X-ray image is displayed on a computer screen as a background image for the standard 3D model. The standard 3D model is then rotated, translated and scaled by a technician to match the orientation of the X-ray image. Then the individual teeth are adjusted to match those in the X-ray. However, the model generated by conventional methods is not an exact model of the patient's teeth but merely an approximate model of the patient's teeth because instead of actual patient teeth, standard teeth are used. Hence, the patient's progress cannot be accurately tracked and reliable data is unavailable to manufacture adjustment appliances.

Therefore, a system and method for detecting deviations from a prescribed course of treatment to gradually reposition teeth to a pre-existing prescribed tooth arrangement; and accurately tracking the progress of a patient's teeth are needed.

SUMMARY OF THE INVENTION

In one embodiment, a method for detecting and correcting deviation during an orthodontic treatment plan is provided. The method includes the steps of receiving an un-segmented current teeth image representing a patient's teeth after an orthodontic treatment plan has begun and before the plan ends for the patient; matching a previously segmented teeth model with the current teeth image; and generating at least one corrective stage to define an intermediate tooth arrangement, wherein the at least one corrective stage repositions a digital teeth image so that a prescribed tooth arrangement of the previously segmented teeth model can be used.

This brief summary has been provided so that the nature of the disclosure may be understood quickly. A more complete understanding of the disclosure can be obtained by reference to the following detailed description of the various embodiments thereof in connection with the attached drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The foregoing features and other features of the present disclosure will now described with reference to the drawings of the various embodiments. In the drawings, the same components have the same reference numerals. The illustrated embodiments are intended to illustrate, but not to limit the disclosure. The drawings include the following Figures:

FIG. 11 is a screen shot of a dialog box for displaying the teeth with a matching error greater than pre-determined parameters, according to one embodiment of the present disclosure;

FIG. 15 is a screen shot of a message warning the technician that at least one tooth is over the acceptable matching surface limit, according to one embodiment of the present disclosure.

DETAILED DESCRIPTION OF THE INVENTION

Figure 1:
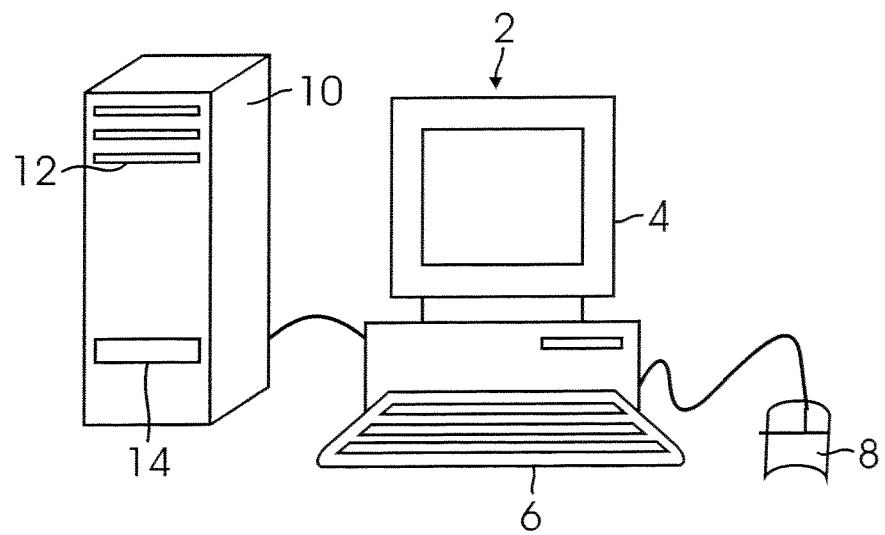
FIG. 1 shows a block diagram of a computing system for executing process steps, according to one embodiment of the present disclosure.

The following definitions are provided as they are typically (but not exclusively) used in the computing and orthodontics environment, implementing the various embodiments disclosed herein.

"Corrected Stages" means creating new stages from a Previously Segmented Teeth Model(s) stage by causing the teeth in the Previously Segmented Teeth Model to move from a Current Teeth Image to the same position in a pre-existing Prescribed Tooth Arrangement or one of the pre-existing stages of a Previously Segmented Teeth Model so that the Prescribed Tooth Arrangement established by the Previously Segmented Teeth Model can be used and will not change. Before any new Corrected Stages can be digitally created, a stage of the Previously Segmented Teeth Model for the patient captured by the Current Teeth Image is selected and then adjusted to match the Current Teeth Image. In one embodiment, a pre-existing stage corresponds to a previous appliance worn by the patient or an appliance that was intended to be worn at some time after the previous appliance was worn, but before the Prescribed Tooth Arrangement. By correcting the patient's teeth to the pre-existing Prescribed Tooth Arrangement, a set of new appliance are provided to the patient, although a last appliance will provide the same Prescribed Tooth Arrangement as initially provided. By correcting the patient's teeth to a pre-existing stage, the Prescribed Tooth Arrangement will not change and any pre-existing appliances may be used, which saves time and money to digitally create and physically manufacture new appliances or a new prescribed tooth arrangement.

"Current Teeth Image" means a digital image (two dimensional or three dimensional) representing a patient's teeth at any time after beginning treatment but prior to the teeth being in a Prescribed Tooth Arrangement. The image can be taken from a dental impression, a 2D image (such as a camera picture) and a bite registry, multiple 2D images, intra-oral scan of low or high resolution, X-ray, cone scan, CT-scan, and other methods. The Current Teeth Image may be a digital model but may not be segmented, which is a labor intensive process step. The Current Teeth Image should provide or enable, by software, a certain level of clarity of the teeth so that a Previously Segmented Teeth Model can be adjusted to match the Current Teeth Image.

"Digital Data Set" means any information that may be used to represent a patient's teeth arrangement. This information may be acquired in a plurality of ways, for example (a) by scanning dental impressions which are typically received from a dental laboratory; (b) a patient's teeth may be scanned or imaged using X-Rays, cone scan, computer aided tomographic images; (c) scanning digital pictures of a patient's teeth; (d) scanning and digitizing analog pictures; (e) or any other method.

"Initial Segmented Teeth Model" means the Initial Segmented Teeth Model that is created at the beginning of a patient's treatment plan.

"Prescribed Tooth Arrangement" means an arrangement of a patients teeth at the end of a treatment plan, created from an Initial Segmented Teeth Model.

"Previously Segmented Teeth Model" means a digital 3D segmented model that provides specific incremental stages of segmented teeth arrangement to move teeth from the Initial Segmented Teeth Model to the Prescribed Tooth Arrangement. The Previously Segmented Teeth Model is created before the Current Teeth Image is available. By comparing a Previously Segmented Teeth Model to the initial Corrected Stage, a patient's progress during an orthodontic treatment plan can be tracked and any deviation from the desired treatment path can be detected by a technician well before a doctor or a patient could recognize the deviation or understand that it could hinder or prevent the most effective and efficient Prescribed Tooth Arrangement.

"Segmented Teeth Model" means a digital 3D model that has been segmented so that each tooth may be represented as a separate digital object. The segmentation step is performed by software and is labor intensive.

"Teeth Model" means a digital 3D model incorporating dental information associated with a patient's teeth. Typically, the model is based on the Digital Data Set.

In one embodiment, the present disclosure provides a system and method for detecting deviations from a prescribed course of treatment to gradually reposition teeth. When a patient's orthodontic treatment begins a Segmented Teeth Model is generated and used to create a set of stages (e.g., pre-existing stages) from the Initial Segmented Teeth Model to the Prescribed Tooth Arrangement. From the set of pre-existing stages, a set of incremental adjustment appliances are created to move the patient's teeth into a prescribed tooth arrangement. However, a patient's teeth may stray from the planned course of treatment. This can be as a result of unforeseen physical traits of a patient's teeth or prolonged periods of non-use of the appliances by the patient, or some other reason. As a result, one or more appliances will have a geometry that is inoperative or uncomfortable to wear by the patient. To correct these deviations, which may occur at any stage of treatment a Corrected Stage or stages are created which will position the patient's teeth to conform to a pre-existing stage or the pre-existing Prescribed Tooth Arrangement. New appliances are generated from the corrected stage or stages. If the generated appliances manufactured from the Corrected Stages do not bring the patient's teeth directly to the pre-existing Prescribed Tooth Arrangement, they will bring the patient's teeth back in the position of a pre-existing stage so that the already created appliances can continue to be used to move the patient's teeth into the Prescribed Tooth Arrangement.

There are a number of reasons why the Corrected Stages may move the teeth directly to the pre-existing Prescribed Tooth Arrangement, thereby avoiding the use of pre-existing appliances made from the Previously Segmented Teeth Model. For example, the Current Teeth Image may present some new treatment difficulties that cannot be effectively and efficiently resolved by the remaining pre-existing appliances, so a new set of appliance will need to be created from the Corrected Stages to reach the Prescribed Tooth Arrangement. On the other hand, logistically, from a distribution aspect, it may be easier and less confusing to send the doctor a new complete set of appliances from the Corrected Stages than to ask the doctor or patient to integrate a few new appliances from the Corrected Stages into the pre-existing appliances from the Previously Segmented Teeth Model.

The system can be implemented in software and executed by a computing system. To facilitate an understanding of the preferred embodiment, the general architecture and operation of a computing system will be described first. The specific process under the preferred embodiment will then be described with reference to the general architecture.

FIG. 1 is a block diagram of a computing system for executing computer executable process steps according to one embodiment of the present disclosure. FIG. 1 includes a host computer 2 and a monitor 4. Monitor 4 may be a CRT, a LCD, a plasma, or any other type of color or monochrome display. Also provided with computer 2 are a keyboard 6 for entering data and user commands, and a pointing device (for example, a mouse) 8 for processing objects displayed on monitor 4.

Computer 2 includes a computer-readable memory storage device 10 for storing readable data. Besides other programs, storage device 10 can store application programs including web browsers and computer executable code, according to the present disclosure.

According to one embodiment of the present disclosure, computer 2 can also access computer-readable removable storage devices storing data files, application program files, and computer executable process steps embodying the present disclosure or the like via a removable memory device 12 (for example, a CD-ROM, CD-R/W, flash memory device, zip drives, floppy drives and others).

It is noteworthy that the present disclosure is not limited to the FIG. 1 architecture. For example, notebook or laptop computers, or any other system capable of connecting to a network and running computer-executable process steps, as described below, may be used to implement the various aspects of the present disclosure.

Figure 2:
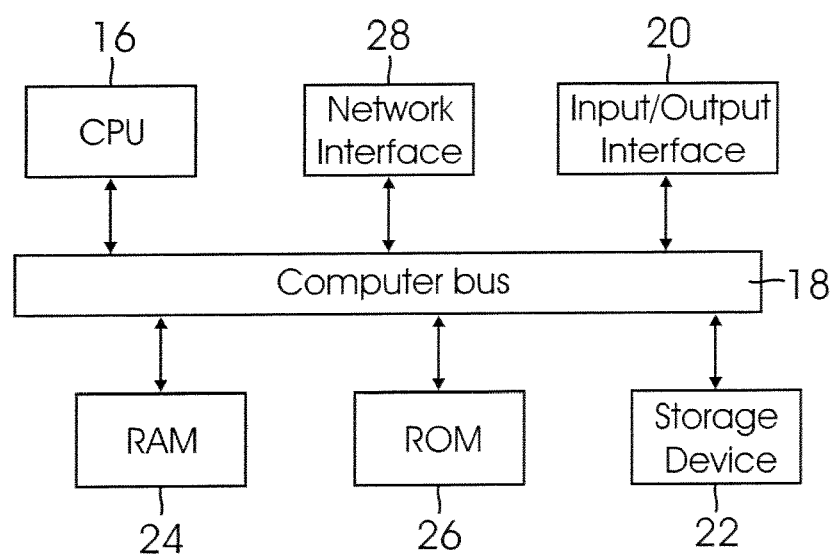
FIG. 2 shows the internal architecture of the computing system of FIG. 1.

FIG. 2 shows a top-level block diagram showing the internal functional architecture of computing system 2 that may be used to execute the computer-executable process steps, according to one embodiment of the present disclosure. As shown in FIG. 2, computing system 2 includes a central processing unit (CPU) 16 for executing computer-executable process steps and interfaces with a computer bus 18.

Also shown in FIG. 2 are an input/output interface 20 that operatively connects output display devices such as monitors 4, input devices such as keyboards 6 and a pointing device such as a mouse 8.

A storage device 22 (similar to device 10) also interfaces with computing system 2 via computer bus 18. Storage device 22 may be disks, tapes, drums, integrated circuits, or the like, operative to hold data by any means, including magnetically, electrically, optically, and the like. Storage device 22 stores operating system program files, application program files, computer-executable process steps of the present disclosure, web-browsers and other files. Some of these files are stored on storage device 22 using an installation program. For example, CPU 16 executes computer-executable process steps of an installation program so that CPU 16 can properly execute the application program.

Random access memory ("RAM") 24 also interfaces with computer bus 18 to provide CPU 16 with access to memory storage. When executing stored computer-executable process steps from storage device 22, CPU 16 stores and executes the process steps out of RAM 24.

Read only memory ("ROM") 26 is provided to store invariant instruction sequences such as start-up instruction sequences or basic input/output operating system (BIOS) sequences.

Computing system 2 can be connected to other computing systems through a network interface 28 using computer bus 18 and a network connection (for example 14). Network interface 28 may be adapted to one or more of a wide variety of networks, including local area networks, storage area networks, wide area networks, the Internet, and the like.

In one embodiment of the disclosure, course correction software may be supplied on a CD-ROM or a floppy disk or alternatively could be read from the network via network interface 28. In yet another embodiment of the disclosure, computing system 2 can load the course correction software from other computer readable media such as magnetic tape, a ROM, integrated circuit, or a magneto-optical disk.

Alternatively, the course correction software is installed onto the storage device 22 of computing system 2 using an installation program and is executed using the CPU 16.

In yet another aspect, the course correction software may be implemented by using an Application Specific Integrated Circuit that interfaces with computing system 2.

Figure 3:
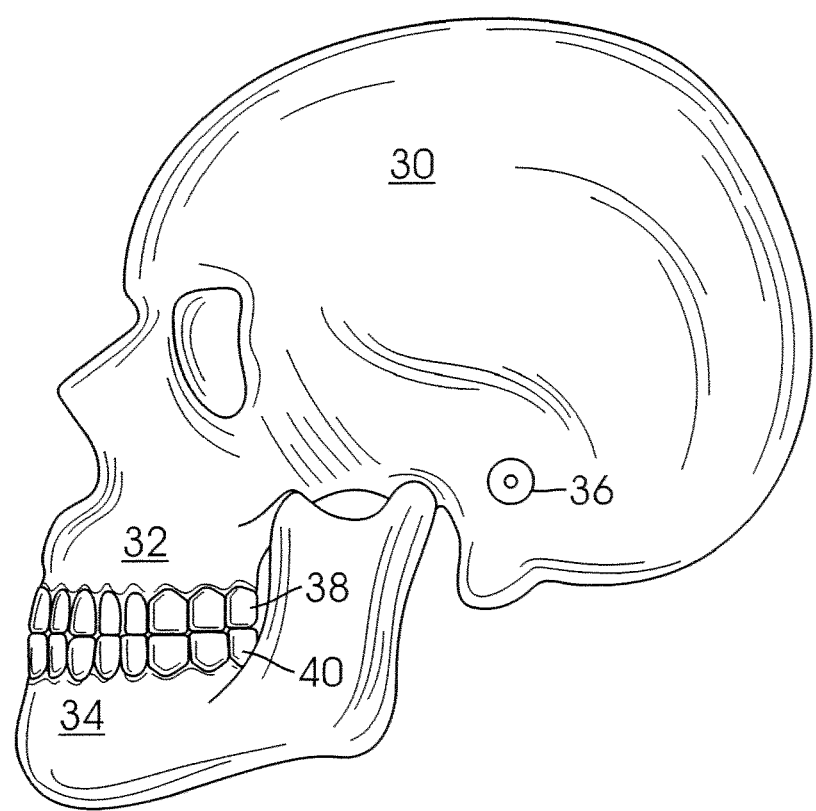
FIG. 3 is an elevational diagram showing the anatomical relationship of the jaws of a patient.

Turning to FIG. 3, a skull 30 with an upper jaw bone 32 and a lower jaw bone 34 is shown. Lower jaw bone 34 hinges at a joint 36 to skull 30. Joint 36 is called a temporal mandibular joint (TMJ). Upper jaw bone 32 is associated with an upper jaw 38, while lower jaw bone 34 is associated with a lower jaw 40.

A computer model of jaws 38 and 40 is generated, and a computer simulation models interactions among the teeth on jaws 38 and 40. The computer simulation allows the system to focus on motions involving contacts between teeth mounted on the jaws and to render realistic jaw movements that are physically correct when jaws 38 and 40 contact each other. The model of the jaw places the individual teeth in a treated position. Further, the model can be used to simulate jaw movements including protrusive motions, lateral motions, and "tooth guided" motions where the path of lower jaw 40 is guided by teeth contacts rather than by anatomical limits of jaws 38 and 40. Motions are applied to one jaw, but may also be applied to both jaws. Based on the occlusion determination, the prescribed tooth arrangement can be ascertained.

Figure 4A:
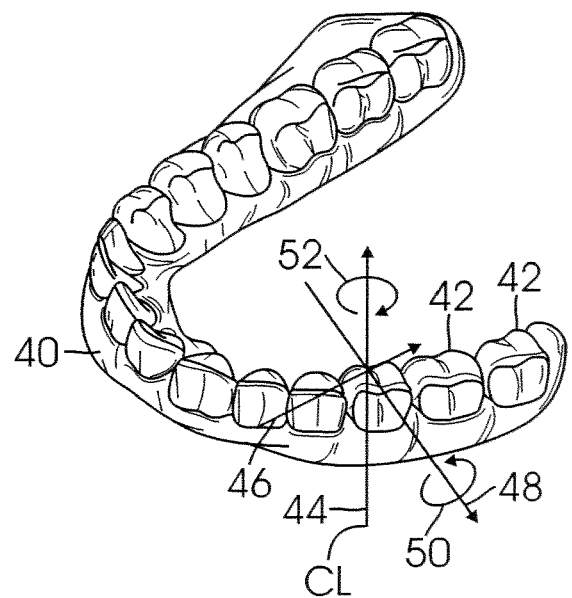
FIG. 4A illustrates in more detail the patient's lower jaw and provides a general indication of how teeth may be moved by the methods and system of the present disclosure.

Referring now to FIG. 4A, lower jaw 40 includes a plurality of teeth 42, for example. At least some of these teeth may be moved from a Previously Segmented Teeth Models to a prescribed tooth arrangement. As a frame of reference describing how a tooth may be moved, an arbitrary centerline (CL) may be drawn through tooth 42. With reference to this centerline (CL), each tooth may be moved in orthogonal directions represented by axes 44, 46, and 48 (where 44 is the centerline). The centerline may be rotated about axis 48 (root angulation) and axis 44 (torque) as indicated by arrows 50 and 52, respectively. Additionally, tooth 42 may be rotated about the centerline, as represented by arrow 52. Thus, all possible free-form motions of the tooth can be performed.

Figure 4B:
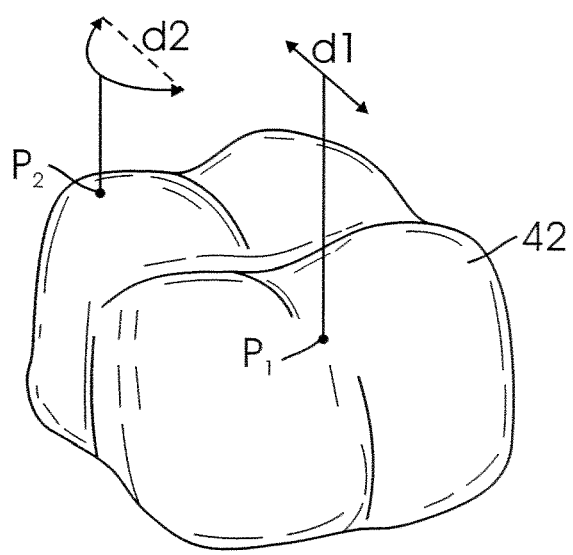
FIG. 4B illustrates a single tooth from FIG. 4A and defines how tooth movement distances are determined.

FIG. 4B shows how the magnitude of any tooth movement may be defined in terms of a maximum linear translation of any point P on tooth 42. Each point P will undergo a cumulative translation as tooth 42 is moved in any of the orthogonal or rotational directions defined in FIG. 4A. That is, while point P will usually follow a nonlinear path, there is a linear distance between any point P in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present disclosure are defined in terms of the maximum permissible movement of point P1 induced on any particular tooth. Such maximum tooth movement, in turn, is defined as the maximum linear translation of point P1 on the tooth that undergoes the maximum movement for tooth 42 in any treatment step.

Figure 5:
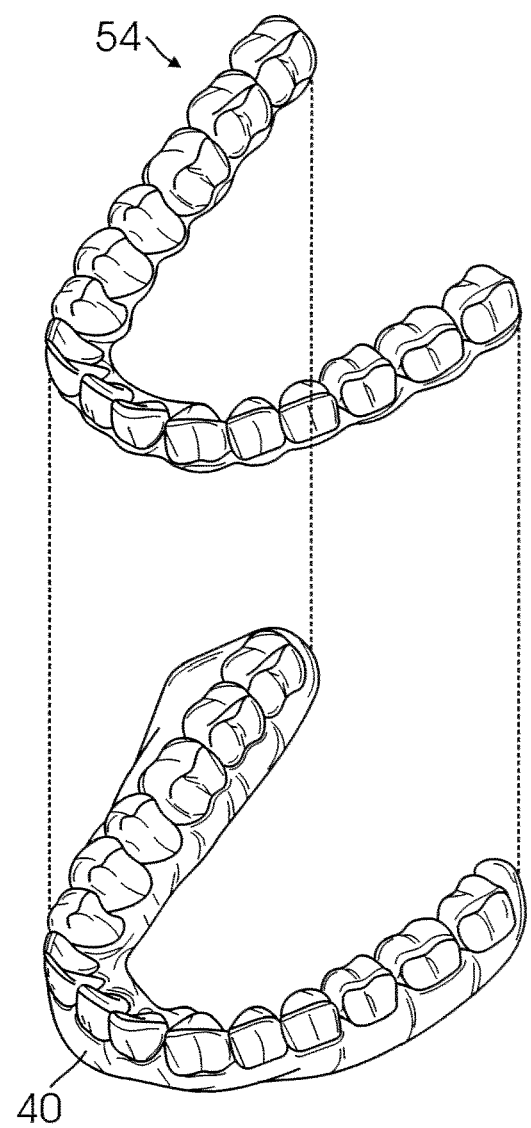
FIG. 5 illustrates the jaw of FIG. 4A together with an incremental position adjustment appliance.

FIG. 5 shows one adjustment appliance 54 which is worn by the patient in order to achieve an incremental repositioning of individual teeth in the jaw as described generally above. Appliance 54 is a polymeric shell having a teeth-receiving cavity. This is described in U.S. Pat. No. 6,450,807, which claims priority from U.S. Pat. No. 5,975,893, which in turn claims priority from provisional application No. 06/050,352, filed Jun. 20, 1997 (collectively the "prior applications"); all of which are assigned to the assignee of the present application, and the disclosures of which are incorporated herein by reference in their entireties.

As set forth in the prior applications, each polymeric shell may be configured so that its tooth-receiving cavity has a geometry corresponding to a pre-existing stage intended for appliance 54. The patient's teeth are repositioned to a prescribed tooth arrangement by placing a series of incremental position adjustment appliances over the patient's teeth. The adjustment appliances are generated at the beginning of the treatment from pre-existing stages generated from an impression taken of the patient's teeth. Ideally, the patient wears each appliance for two weeks or until the pressure of each appliance on the teeth is minimal. At that point, the patient moves onto the next stage of the planned course of treatment and replaces the current adjustment appliance with the next adjustment appliance in the series until no more appliances remain. Conveniently, the appliances are generally not affixed to the teeth and the patient may place and replace the appliances at any time during the procedure.

The polymeric shell 54 can fit over all teeth present in the upper or lower jaw. Typically, only certain one(s) of the teeth will be repositioned while others of the teeth will provide a base or an anchor region for holding appliance 54 in place as appliance 54 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance. [0061] Polymeric appliance 54 of FIG. 5 may be formed from a thin sheet of a suitable elastomeric polymer, such as Tru-Tain 0.03, in thermal forming dental material, available from Tru-Tain Plastics, Rochester, Minn. Typically, no wires or other means will be provided for holding the appliance in place over the teeth. In some cases, however, it will be desirable or necessary to provide individual anchors on teeth with corresponding receptacles or apertures in appliance 54 so that the appliance can apply an upward force on the tooth that would not be possible in the absence of such an anchor.

As discussed above, a patient's teeth may stray from the planned course of treatment. This can be as a result of unforeseen physical traits of a patient's teeth, prolonged periods of non-use of the appliances by the patient or other reasons. As a result, one or more appliances will have a geometry that is undesirable or unable to effectively move teeth to a desired position or stage. Without the system and method of the present disclosure, the dentist would have to start the repositioning process again by taking another impression of the patient's teeth.

The new impression for the re-start process captures the patient's new initial or current position so that a new 3D digital model of the teeth can be created, each tooth defined and segmented, the gingival line formed, and all stages created to effectively move the teeth from a current position to a new prescribed tooth arrangement. The prescribed tooth arrangement is new during a re-start case because the new stages created during this process are never matched to a pre-existing stage or the pre-existing prescribed tooth arrangement, but instead create new stages to reach a new, yet similar, prescribed tooth arrangement. This is described in U.S. Pat. No. 7,077,647, which is assigned to the assignee of the present application, and the complete disclosure of which is incorporated herein by reference.

In contrast, the system and method of the present disclosure allows for adjustment of any teeth that are off track from any of the pre-existing stages to a Corrected Stage(s) to reach the pre-existing Prescribed Tooth Arrangement or a pre-existing stage of the Previously Segmented Teeth Model. The corrected stage or stages are used to create the additional appliances.

Figure 6:
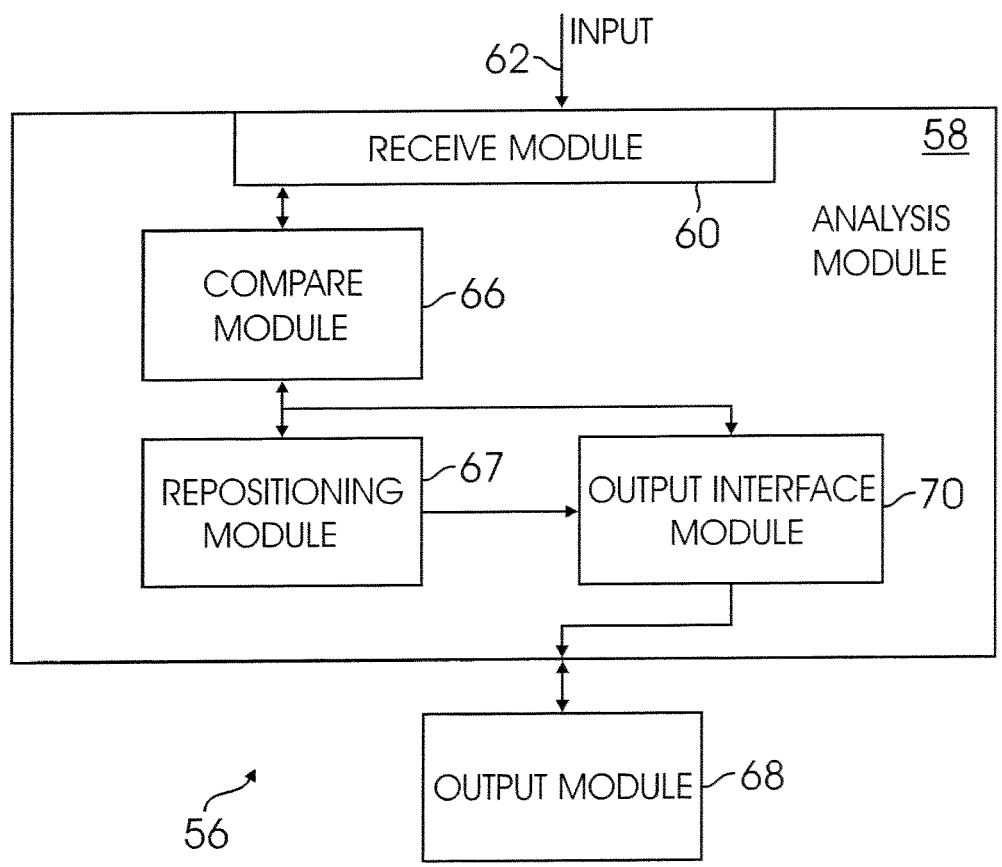
FIG. 6 shows a block diagram of a system for correcting deviations during the prescribed course of an orthodontic treatment to gradually reposition teeth, according to one embodiment of the present disclosure.

FIG. 6 shows a block diagram of a system 56 for correcting deviations from a planned orthodontic treatment course to gradually reposition teeth, according to one embodiment of the present disclosure. System 56 comprises an analysis module 58 having a receive module 60 for receiving input data 62. Input data 62 includes (1) Current Teeth Image; and (2) Previously Segmented Teeth Model.

A technician obtains a Previously Segmented Teeth Model or an Initial Segmented Teeth Model that was created from the initial impression of the patient's teeth taken at the beginning of the orthodontic treatment. The technician can use any stage of the Previously Segmented Teeth Model. For tracking purposes and analysis to correct similar deviations in the future, the technician will typically use the stage of the Previously Segmented Teeth Model that is most closely related to the Current Teeth Image. In other words, the stage Previously Segmented Teeth Model for the last appliance worn or next to be worn is likely to be used.

The Current Teeth Image may be generated from an impression of the patient's teeth, a 2D image (such as a camera picture) and a bite registry, multiple 2D images, intraoral scan of low or high resolution, X-ray, CT-scan and others taken during the course of the treatment. A technician pre-processes the Current Teeth Image, prior to being input into receive module 6 by manually assigning a unique Facial Axis of the Clinical Crown (FACC), a unique current identifier (e.g., abnormalities in a tooth or attachments or markers placed on a tooth), or by using a cusp or surface matching algorithm, to each tooth. Each tooth in the Previously Segmented Teeth Model is already assigned a unique starting identifier like FACC.

A compare module 66, within analysis module 58, compares the Current teeth Image with the Previously Segmented Teeth Model to determine if there is an initial match. To determine if there is an initial match, the Current teeth Image with the Previously Segmented Teeth Model are overlaid on each other and the relative location of each tooth is identified by its unique identifier or FACC. If no mismatches are generated, an initial match occurs. The initial match confirms that the technician is using the correct Previously Segmented Teeth Model for the Current Teeth Image.

A mismatch occurs if there are any teeth numbering irregularities, for example, the total number of teeth in each model is not the same, or at least one tooth is missing a FACC.

A technician reviews mismatch details and corrects the mismatch(es) by manually adjusting or repositioning each tooth with a mismatch using the Previously Segmented Teeth Model or adjusting information relating to each tooth with a mismatch, as described below. By knowing a current location of each tooth, the difference between the current location and a previous location can be measured and tracked to understand the adjustments made and possibly how to prevent a similar deviation in the future. In addition, based on this distance, the technician uses the Previously Segmented Teeth Model to move or reposition each tooth with a mismatch from its present location to a desired location.

When the technician adjusts the Previously Segmented Teeth Model, the adjustment data is input into receive module 60 and sent to repositioning module 67 which receives the data via compare module 66. Repositioning module 67 uses this data to reposition the teeth with mismatches. When the mismatches have been corrected, the corrected stages are transmitted back to compare module 66 and the process is repeated until an initial match is achieved. The initial match provides a good starting position for the next step in the process, matching the surfaces of the corresponding teeth.

After an initial match is achieved, compare module 66 executes a surface matching algorithm which prompts the technician to enter bite match settings. Bite match settings include pre-determined tolerances and the number of times a surface matching algorithm can be executed, as described below with reference to FIG. 10. Any tooth from the Previously Segmented Teeth Model that is found to be within a pre-set tolerance away from the starting position is a good surface match and the tooth is repositioned accordingly.

The surface matching algorithm takes a number of samples of each tooth in the Previously Segmented Teeth Model and finds the closest corresponding sampling point on the jaw image in the Current Teeth Image. A grid is created on each tooth and the number of samples is randomly selected and then the grid is overlaid on the Current Teeth Image. This is done as the Current Teeth Image needs to match the Previously Segmented Teeth Model. If the match is off by a millimeter, when repositioned to match the data, the tooth is also off by a millimeter. This process is done iteratively until the deviations are below a certain threshold of the overall point data set differences.

Repositioning module 67 allows a technician to utilize a Previously Segmented Teeth Model of the patient's teeth to reposition each tooth that has a mismatch or deviation above pre-determined tolerances. Thus, a technician does not need to go through the laborious process of creating a segmented tooth model for the Current Teeth Image. Consequently, the Current Teeth image may be a lesser quality image or format as long as the resolution is high enough to allow the matching process.

When repositioning is completed, the Corrected Stages are communicated to an output module 68 via an output interface module 70 within analysis module 58. Output module 68 may be any device with a monitor or any device capable of receiving a communication.

It is noteworthy that analysis module 58 may be implemented in software code or by using application specific integrated circuits (ASIC). The present adaptive aspects are not limited to the modular structure shown in FIG. 6, more or fewer components may be used to implement module 58.

Figure 7:
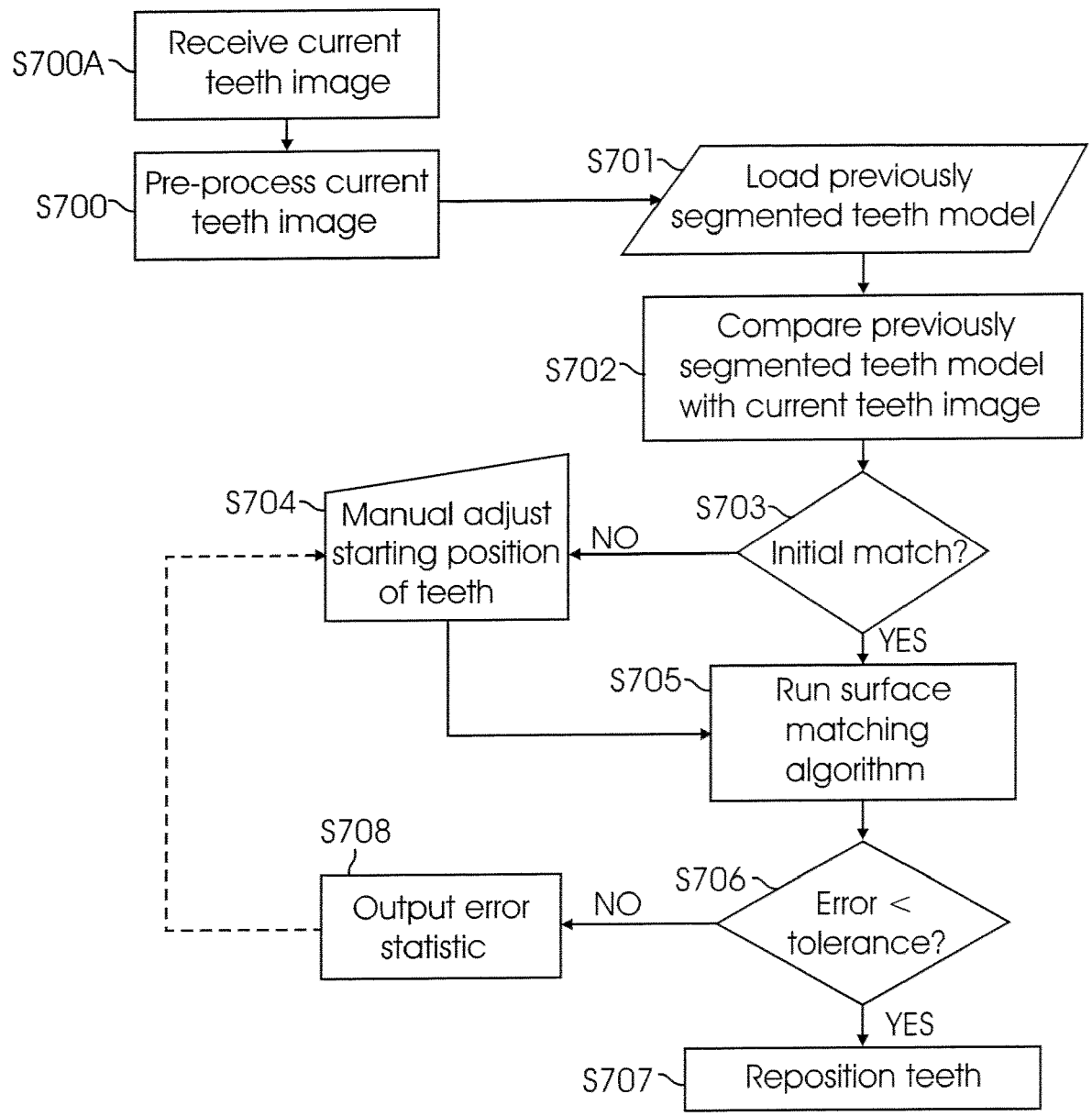
FIG. 7 is a flow chart showing the steps of correcting deviations during a prescribed course of treatment to gradually reposition teeth, according to one embodiment of the present disclosure.

FIG. 7 is a flow chart showing the steps of detecting deviations from a planned course of treatment to gradually reposition teeth, according to one embodiment of the present disclosure. The process starts in step S700A, when a Current Teeth Image is received or obtained by a technician.

In step S700, the Current Teeth Image is pre-processed using a digital data software tool and each tooth is assigned a Facial Axis of the Clinical Crown (FACC), i.e. a unique current identifier, with jaw characteristics set. In one embodiment, the Current Teeth Image does not need to be segmented, which saves a technician's time and hence reduces overall cost for processing digital teeth data.

In step S701, a Previously Segmented Teeth Model is selected, and is input into system 56 of FIG. 6 with the Current Teeth Image. Depending on the stage, the Previously Segmented Teeth Model may be the Initially Segmented Teeth Model, the Prescribed Tooth Arrangement or some stage there between.

In step S702, the Previously Segmented Teeth Model and the Current Teeth Image are compared. An initial matching algorithm is executed which matches the unique starting identifiers (FACCs) of each tooth in the Previously Segmented Teeth Model to the respective unique current identifiers (FACCs) of each tooth in the Current Teeth Image as assigned in step S700. The images are overlaid on each other and the relative location of each tooth is identified by its unique identifier (or FACC) to determine if there are any mismatches in step S703. The initial matching process is performed to determine if there is a gross mismatch so that a technician does not waste time in performing surface matching (step S705) that is described below.

If any mismatches are found, an initial match has not occurred and the mismatches are displayed in the form of an informational dialog that provides details of the mismatches, such as teeth numbering irregularities or missing FACCs. A mismatch occurs if there are any teeth numbering irregularities, for example, the total number of teeth in each model is not the same, or at least one tooth is missing a FACC.

In step S704, a technician manually adjusts or repositions each tooth with a mismatch using the Previously Segmented Teeth Model or adjusts the information relating to each tooth with a mismatch. By knowing a current location of each tooth, the distance between the current location from a starting location can be measured. Based upon this distance, the technician uses the Previously Segmented Teeth Models to move or reposition each tooth with a mismatch from its present location to the desired location creating corrected stages. Thereafter, the process moves to step S705 that is described below.

If no mismatches are generated in step S703, then an initial match occurs and the process moves to step S705. The initial match confirms that the technician is using the correct Previously Segmented Teeth Model and the Current Teeth Image, which provides a good starting point for executing a surface matching algorithm. It is noteworthy that although the process steps S702 (initial matching) and S705 (surface matching) are shown as separate steps, they may be performed in a single step.

In step S705, system 56 (see FIG. 6) executes a surface matching algorithm. The surface matching algorithm takes a number of samples of each tooth in the Previously Segmented Teeth Model and finds the closest corresponding sampling point on the Current Teeth Image. A grid is created on each tooth and the number of samples is randomly selected and then the grid is overlaid on the Current Teeth Image.

In step S706, any resulting errors from the surface matching algorithm are compared to predetermined tolerances (as described below with reference to FIG. 10) to determine if the resulting errors are less than the predetermined tolerance. If the resulting errors are less than the pre-determined tolerance, then in step S707, the teeth in the Previously Segmented Teeth Model are repositioned corresponding to a corrected stage.

If the resulting errors are greater than the pre-determined tolerance, then in step S708, error statistics for the surface matching algorithm is output to a display device. The display provides suggestions to perform certain steps to get a better match. In some cases, a technician may manually adjust the teeth that did not match in step S706. After the manual adjustment, the process moves back to step S705 and the surface matching algorithm is re-run.

It is noteworthy that although it is convenient to perform the initial matching step, a technician may choose to perform only the surface matching step and based on the results manually adjust the teeth and then re-run the surface matching step.

It is noteworthy that the adaptive aspects disclosed herein allows one to track the adjustments made to each tooth of the Previously Segmented Tooth model to match the Current Teeth Image. Furthermore, one can create Corrective Stages with the Previously Segmented Teeth model from a tooth arrangement of a Current Teeth Image to a Prescribed Tooth Arrangement or a Previously Segmented Teeth model.

Figure 8:
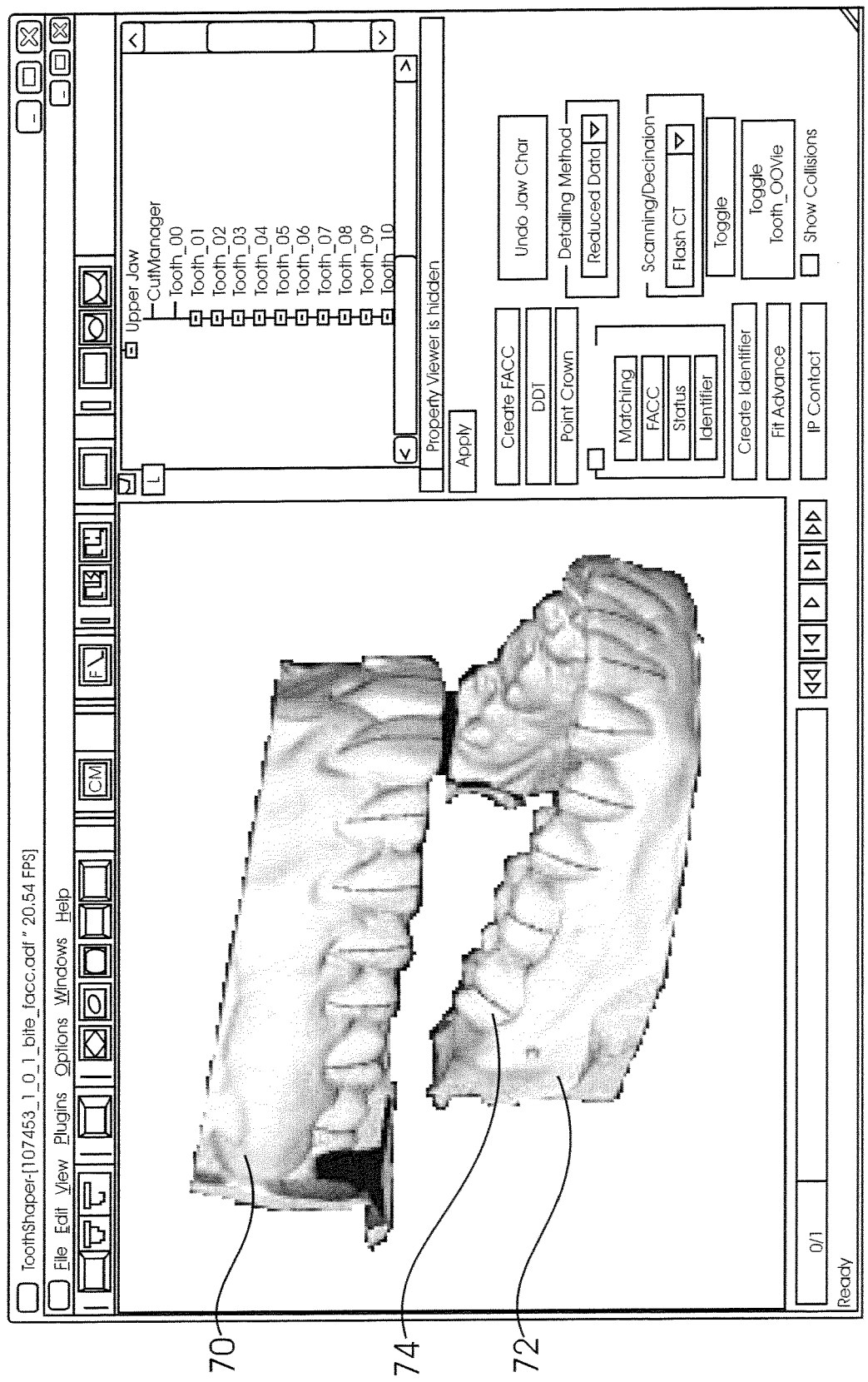
FIG. 8 is a screen shot showing a graphical representation of a three-dimensional model of a patient's upper and lower jaws based on a current digital data set, according to one embodiment of the present disclosure.

FIG. 8 is a screen shot showing a graphical representation of a three-dimensional model of a patient's upper and lower jaws 70, 72 generated from a Current Teeth Image. As described above, using a digital detailing tool (DDT), a technician pre-processes the Current Teeth Image by assigning and placing FACC's or unique current identifiers 74 on each tooth in the model. Unique current identifiers are landmarks on the teeth for the purposes of matching which include attachments or specific characteristics of a tooth. Each FACC has a number associated with it and that is the tooth number, so the same tooth from the Previously Segmented Teeth Models and the Current Teeth Image should be in a similar location.

Figure 9:
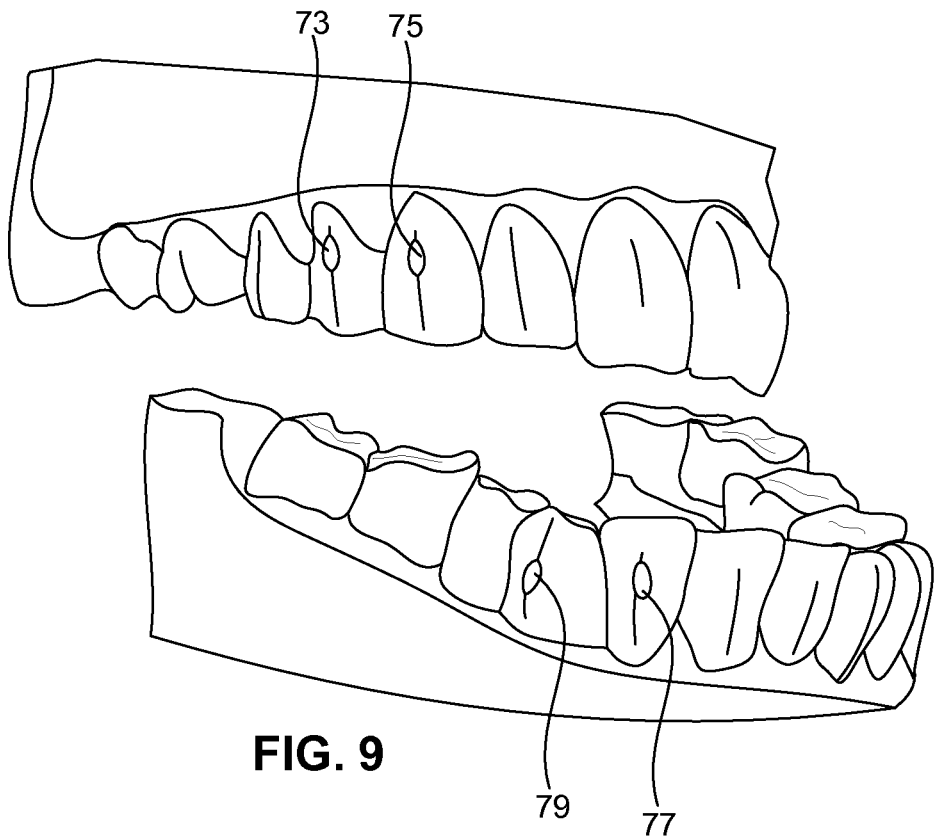
FIG. 9 is a graphical representation of a three-dimensional model of an initial match that can occur when the three dimensional model of digital translated images are overlaid on three dimensional model of the Current Teeth Image, according to one embodiment of the present disclosure.

FIG. 9 is a graphical representation of a three-dimensional model of an initial match (step S703, FIG. 7) that may occur when a Previously Segmented Teeth Model is overlaid on the Current Teeth Image, according to one embodiment of the present disclosure. The initial match provides a starting position for subsequent surface matching so that a good match is achieved.

If the initial matching algorithm determines that one or more teeth are mismatched, the initial matching algorithm cannot complete the initial matching satisfactorily because of teeth numbering irregularities or missing FACCs. In this instance, the initial matching algorithm will generate an informational dialog giving details of the mismatches allowing the technician to correct them and execute the initial matching algorithm again. Also shown in FIG. 9 are four attachments 73, 75, 77, 79 that have been added to four of the patient's teeth. An attachment assists to anchor an appliance to a tooth, assist in moving a tooth to a desired position or correct imperfections in a tooth, such as uneven surfaces, so that the appliances will fit properly.

Figure 10:
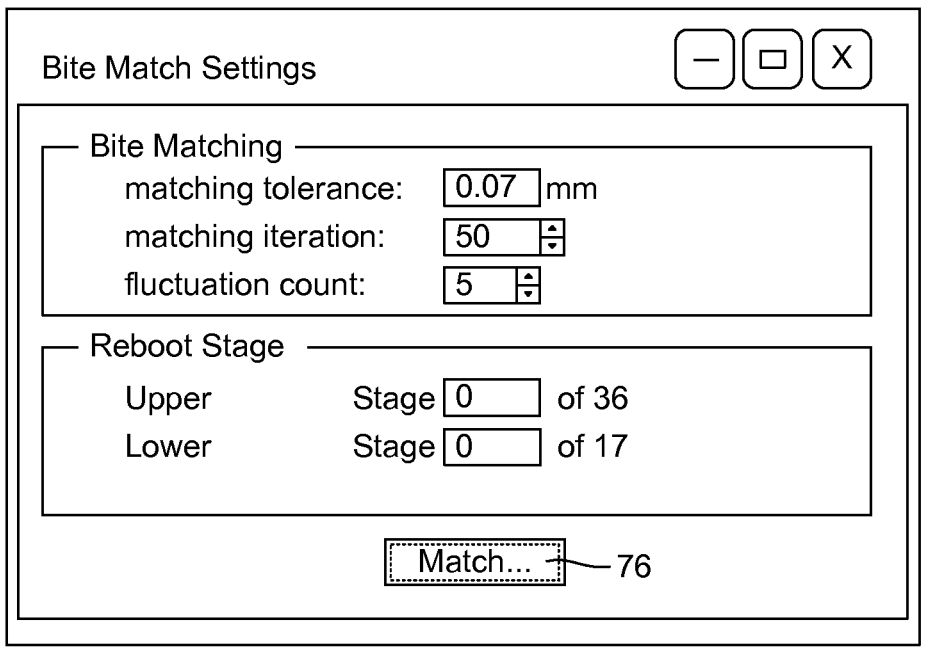
FIG. 10 is a screen shot of a menu for entering bite match settings, according to one embodiment of the present disclosure.

FIG. 10 is a screen shot of a menu for entering bite match settings, according to one embodiment of the present disclosure for performing the surface matching process step S705 (FIG. 7). Upon selecting the surface matching algorithm, a menu for entering bite match settings is displayed prompting the technician to enter the bite matching settings. The bite matching settings are pre-determined parameters or tolerances. The pre-determined tolerances include (1) a matching tolerance which defines when the tooth and the Current Teeth Image surfaces qualify as a match; (2) a maximum iteration which is the number of matching iteration steps that the algorithm is allowed to run; (3) a fluctuation count which defines the number of steps allowed before the algorithm is stopped as an error is not reduced (sometimes the matching algorithm runs into a local surface matching minimum and can not minimize further to achieve the tolerance as the starting positioning is not good enough, or there is a discrepancy between the Previously Segmented Teeth Model and the Current Teeth Image); and (4) reboot stage information is taken from the RX (or original planned course of treatment as determined by an orthodontist) and used for two types of course correction, reboot and refinement.

With reboot, the patient has not completed treatment, but the appliances no longer fits. Each stage in the reboot represents an appliance in the series of appliances. The technician enters the stage for both the upper and lower teeth where the teeth have strayed from the planned course of treatment.

With refinement, the patient has completed the planned course of treatment, but the teeth were not repositioned as expected. In other words, the patient has used all the appliances but the teeth still require repositioning requiring the patient to start from the beginning of the process.

Once the technician has entered the pre-determined tolerances, the technician selects a match button 76 causing the surface matching algorithm to be executed (step 5705, FIG. 7). During this process each tooth in the Previously Segmented Teeth Model is matched with the corresponding tooth in the Current Teeth Image. If a tooth from the Previously Segmented Teeth Model is found to be within a pre-set tolerance away from the Current Teeth Image, it determined (or concluded) that a good match is found and the program positions the tooth to this new matching transform to create a corrected set of stages.

When the matching operation is complete the results are displayed in an interactive dialog box (or user-interface) (81), as shown in the screen shot of FIG. 11. Dialog box 81 includes a top segment 81A that displays teeth which were not matched. A user can select a particular tooth, for example, tooth number 4 (shown in dotted rectangle 81B). This generates a report on the selected tooth. The report is shown as segment 81C and labeled as Advanced Properties.

The report identifies the error type (for example, 37 Collision statistics mismatch. Was 0.2969 mm (now 0.0906 mm); the distance a tooth needs to move to create a good match and a suggestion on how to correct the error. Suggestions are generated by using a current matching distance and the type of error status (for example, "collision statistics mismatch") for each tooth. For example, segment 81C shows the average matching distance to be 0.0694 and the software interface tells the technician to lower the distance to be within 0.030 mm. The technician can reposition the mismatched teeth (step S704) and select the "re-match" option (shown by box 82). This re-runs the surface matching algorithm.

Dialog box 81 also includes a "Trim colliding teeth automatically" checkbox 80, which allows the technician to indicate if a corrected bite (for example, stage 0 in one of the corrected stages) includes any stripped teeth as the starting (un-stripped) teeth. If the stripped teeth are matched, they can cause severe hard collisions. Selecting option 80 automatically trims colliding teeth.

When the matching is complete and matching errors for each tooth are below the parameters defined by the technician, each tooth from the Previously Segmented Teeth Model are translated and rotated to create a corrected stage. The teeth are repositioned in stages, where each appliance in the series of appliances represents a stage. Upon completion of the surface matching program, the corrected stage with an overlay of the corrected stages is displayed to provide visual feedback on the accuracy of the matching. After all the teeth have been matched, or when the technician decides the match is good enough, the technician selects done button 78 causing the Previously Segmented Teeth Models to be automatically deleted.

When no match is found, the matching program is terminated when either the maximum fluctuation count is reached or the maximum iteration is reached. Upon termination, a dialog box is generated identifying the teeth with a matching error greater than the pre-determined tolerances.

As described above, the surface matching algorithm takes a number of samples of the Previously Segmented Teeth Model and finds the closest corresponding sampling point on the jaw image in the Current Teeth Image. A grid is created on each tooth and the number of samples is randomly selected and then the grid is overlaid on Current Teeth Image. This is done as the Current Teeth Image needs to match the Previously Segmented Teeth Model. This process is done iteratively until the deviations are below a certain threshold of the overall point data set differences.

The surface matching algorithm takes each grid and randomly selects, points and superimposes them. The number of points selected is the number of data points that are to be measured. Once all the points have been selected and measured, they are superimposed onto the starting teeth setting and if all the differences on average are below a threshold set by the technician (for example 0.07 mm), then there is a close match.

Both the Previously Segmented Teeth Model and the Current Teeth Image have different frames of reference, so in some cases it is possible to not get a good match. Different frames of reference can occur as a result of lost enamel, a chipped tooth or a bad impression (air bubble).

When the surface matching algorithm is executed, the parts or teeth that did not get a good match are displayed. When there are mismatches, the technician then manually repositions the teeth in the Previously Segmented Teeth Model (step 5704, FIG. 7) and re-runs the initial matching algorithm for the teeth with the errors. (The Current Teeth Image cannot be moved as it is merely a mesh of data.) After re-running the initial matching algorithm, any mismatches (or errors) are displayed and technician evaluates whether or not the errors are acceptable.

Figure 12:
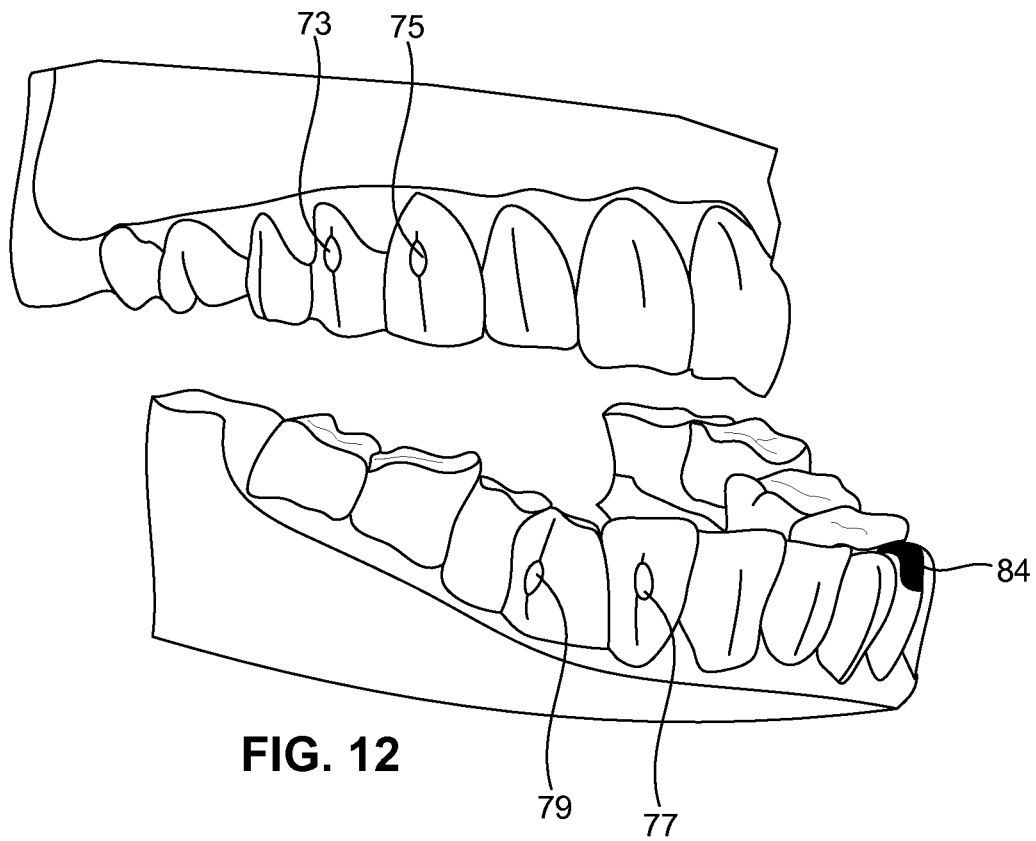
FIG. 12 is a graphical representation of a three-dimensional model of a patient's upper and lower jaw with a matching error, according to one embodiment of the present disclosure.

FIG. 12 is a graphical representation of a three-dimensional model of the patient's upper and lower jaw with a matching error, according to one embodiment of the present disclosure. The teeth with matching errors are marked 84 for easy identification.

Figure 13:
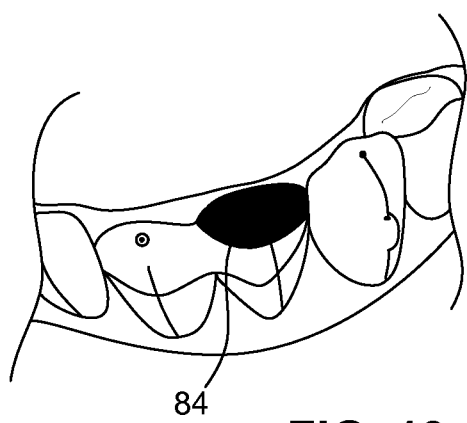
FIG. 13 is an enlarged view of a portion of the jaw in FIG. 12 showing the matching error to be corrected.

A better starting positioning for the matching algorithm needs to be obtained for the teeth identified in the dialog box 81 (FIG. 11). To obtain a better starting positioning, the technician manually adjusts each tooth marked 84 from the Previously Segmented Teeth Model to the desired location on the corrected stages. FIG. 13 is a screen shot of an enlarged view of a portion of the jaw in FIG. 12 showing matching error 84.

Figure 14:
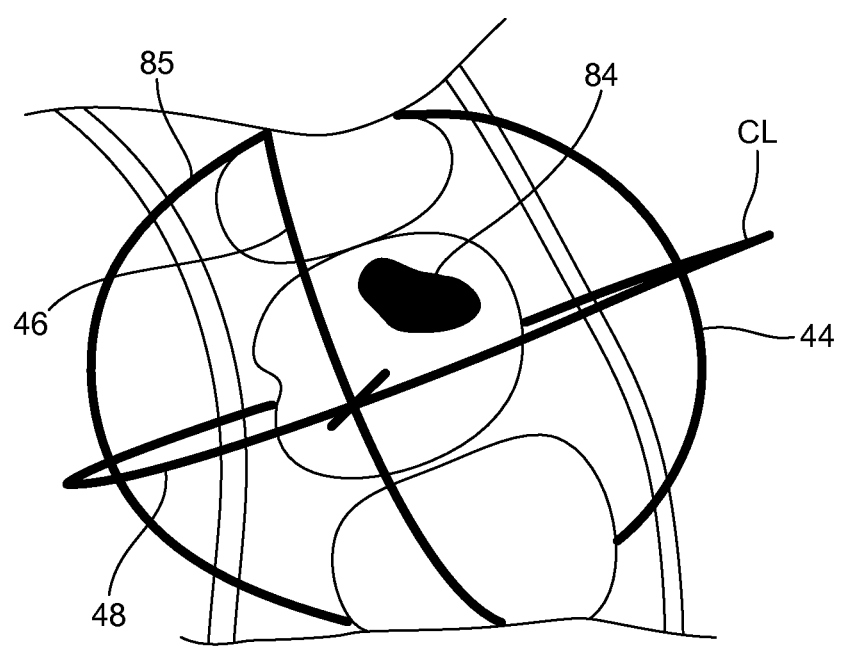
FIG. 14 is an enlarged top view of a portion of the jaw in FIG. 12 showing the matching error to be corrected.

FIG. 14 is an enlarged top view of a portion of the jaw in FIG. 12 showing the matching error 84. As described with reference to FIG. 4, a tooth is re-positioned by drawing an arbitrary centerline CL through the tooth to be re-positioned. With reference to centerline (CL), tooth 84 may be moved in orthogonal directions represented by axes 44, 46, and 48. The centerline may be rotated about axis 48 (root angulation) and axis 44 (torque). Additionally, the tooth may be rotated about the centerline allowing all possible free-form motions of tooth 84 to be performed. A guidance box 85 is placed over the tooth 84 with matching error and is used as a tool to guide the repositioning of the tooth.

After completing individual teeth matching, the technician selects done button 78 in the dialog box shown in FIG. 11 to finish the bite matching process. The program will then compare the teeth matching result to a stoppage limit to make sure that the teeth are matched within tolerance and automatically adjust the gingiva and copy the original final setup into the current case setting. In the preferred embodiment of the present disclosure, the limit for all teeth, except the last molars, are set at default 0.1 mm, last molars limit is set at 0.15 mm.

FIG. 15 is a screen shot of a message warning the technician that at least one tooth is over the acceptable matching surface limit, according to one embodiment of the present disclosure. If any teeth are over the acceptable matching surface limit (0.1 mm), a warning message is generated telling the technician to re-match the listed teeth to prevent the creation of unfitted aligners. If the technician attempts to finish a case while there are still teeth over the limit by selecting a 'NO' button 86, the program will prevent the technician from finishing the case by automatically closing the file, after asking the technician to re-cut the case.

It is possible in some cases that the dialog box of FIG. 11 may display a large number of teeth that cannot be matched. For those cases the following steps would be performed until a satisfactory result is obtained:

(1) If the initial matching was checked and was satisfactory, then the parameters of the matching might have been too restrictive for the particular case and it may be necessary to modify the parameters with a greater tolerance and re-run the matching algorithm again;

(2) An impression discrepancy might contribute to the resulting errors. In this case, the technician might decide that the current errors are acceptable and the teeth would actually be in approximately the correct position (or the same position if the case was re-cut on the corrected bite);

(3) Have excess material removed from the starting impression, and start again by executing the rough bite matching algorithm; and (4) Begin the treatment process again as bite matching is not possible.

In one embodiment, since segmentation is not performed on a Current Teeth Image, it reduces time for a mid-course correction.

In another embodiment, the Previously Segmented Teeth Model of a patient's teeth is used to detect deviations from the planned course of treatment which can occur at any stage during the treatment. By adjusting any teeth that are off track in the Previously Segmented Teeth Model, a corrected set of stages can be created. Additional appliances are generated from the corrected set of stages. The additional appliances will reposition the patient's teeth to the pre-existing Prescribed Tooth Arrangement or a pre-existing stage so that the remainder of the appliances can be used to obtain the prescribed tooth arrangement.

While the present disclosure is described above with respect to what is currently considered its preferred embodiments, it is to be understood that the disclosure is not limited to that described above. To the contrary, the disclosure is intended to cover various modifications and equivalent arrangements within the spirit and scope of the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for tracking movement of a patient's teeth, the computer-implemented method executed by a processing unit coupled to a memory storage device storing code, the computer-implemented method comprising:
    receiving, at a receive module of an analysis module, a three-dimensional previously segmented teeth model of the patient's teeth;
    receiving, at the receive module, a two-dimensional un-segmented teeth image representing a current arrangement of the patient's teeth;
    matching, by a compare module of the analysis module, one or more teeth of the three-dimensional previously segmented teeth model to one or more corresponding teeth of the two-dimensional un-segmented teeth image, wherein the compare module is in communication with the receive module;
    measuring, by the compare module, a distance between a location of a tooth in the two-dimensional un-segmented teeth image and a location of a corresponding tooth in the three-dimensional previously segmented teeth model, by adjusting a position of the tooth in the three-dimensional previously segmented teeth model to the location of the tooth in the two-dimensional un-segmented teeth image; and
    tracking, using the analysis module, a deviation of the tooth in the two-dimensional un-segmented teeth image from an intended position of the tooth in the three-dimensional previously segmented teeth model in a stage of a patient's treatment plan if the distance between the location of the tooth in the two-dimensional un-segmented teeth image and the location of the corresponding tooth in the three-dimensional previously segmented teeth model exceed a pre-determined tolerance.

2. The computer-implemented method of claim 1, wherein the two-dimensional un-segmented teeth image comprises a camera picture.

3. The computer-implemented method of claim 1, wherein the two-dimensional un-segmented teeth image represents an arrangement of the patient's teeth after beginning orthodontic treatment.

4. The computer-implemented method of claim 1, wherein the three-dimensional previously segmented teeth model is generated prior to receiving the two-dimensional un-segmented teeth image.

5. The computer-implemented method of claim 1, wherein the three-dimensional previously segmented teeth model comprises scan data.

6. The computer-implemented method of claim 1, wherein the matching step comprises overlaying the two-dimensional un-segmented teeth image and the three-dimensional previously segmented teeth model onto each other.

7. The computer-implemented method of claim 1, wherein the matching step comprises rotating, scaling, and translating the three-dimensional previously segmented teeth model to represent the two-dimensional un-segmented teeth image.

8. The computer-implemented method of claim 1, wherein the matching step comprises executing a surface matching algorithm.

9. The computer-implemented method of claim 8, wherein the surface matching algorithm comprises:
    creating a grid on the three-dimensional previously segmented teeth model; and
    overlaying the grid onto the two-dimensional unsegmented teeth image.

10. The computer-implemented method of claim 8, wherein the surface matching algorithm comprises:
    selecting one or more sampling points from a tooth in the three-dimensional previously segmented teeth model; and
    identifying one or more corresponding sampling points on the two-dimensional un-segmented teeth image.

11. The computer-implemented method of claim 1, further comprising pre-processing the two-dimensional un-segmented teeth image by assigning a unique identifier to each tooth in the two-dimensional un-segmented teeth image.

12. A system for tracking movement of a patient's teeth, the system comprising:
    a processing unit; and a memory storage device comprising code that, when executed by the processing unit, causes the system to:

generate a three-dimensional previously segmented teeth model of the patient's teeth;

receive a two-dimensional un-segmented teeth image representing a current arrangement of the patient's teeth;

match one or more teeth of the three-dimensional previously segmented teeth model to one or more corresponding teeth of the two-dimensional un-segmented teeth image;

measure a distance between a location of a tooth in the two-dimensional un-segmented teeth image and a location of a corresponding tooth in the three-dimensional previously segmented teeth model, by adjusting a position of the tooth in the three-dimensional previously segmented teeth model to the location of the tooth in the two-dimensional un-segmented teeth image; and tracking a deviation of the tooth in the two-dimensional un-segmented teeth image from an intended position of the tooth in the three-dimensional previously segmented teeth model in a stage of a patient's treatment plan if the distance between the location of the tooth in the two-dimensional un-segmented teeth image and the location of the corresponding tooth in the three-dimensional previously segmented teeth model exceed a pre-determined tolerance.

13. The system of claim 12, wherein the two-dimensional un-segmented teeth image comprises a camera picture.

14. The system of claim 12, wherein the two-dimensional un-segmented teeth image represents an arrangement of the patient's teeth after beginning orthodontic treatment.

15. The system of claim 12, wherein the three-dimensional previously segmented teeth model is generated prior to receiving the two-dimensional un-segmented teeth image.

16. The system of claim 12, wherein the three-dimensional previously segmented teeth model comprises scan data.

17. The system of claim 12, wherein the match step comprises overlaying the two-dimensional un-segmented teeth image and the three-dimensional previously segmented teeth model onto each other.

18. The system of claim 12, wherein the match step comprises rotating, scaling, and translating the three-dimensional previously segmented teeth model to represent the two-dimensional un-segmented teeth image.

19. The system of claim 12, wherein the match step comprises executing a surface matching algorithm.

20. The system of claim 19, wherein the surface matching algorithm comprises:

creating a grid on the three-dimensional previously segmented teeth model; and overlaying the grid onto the two-dimensional unsegmented teeth image.

21. The system of claim 19, wherein the surface matching algorithm comprises:

selecting one or more sampling points from a tooth in the three-dimensional previously segmented teeth model; and identifying one or more corresponding sampling points on the two-dimensional un-segmented teeth image.

22. The system of claim 12, wherein the code further causes the system to pre-process the two-dimensional un-segmented teeth image by assigning a unique identifier to each tooth in the two-dimensional un-segmented teeth image.

23. A computer-implemented method for tracking movement of a patient's teeth, the computer-implemented method executed by a processing unit coupled to a memory storage device storing code, the computer-implemented method comprising:

receiving, at a receive module of an analysis module, a three-dimensional previously segmented teeth model representing an intermediate arrangement of the patient's teeth before tracking movement of the patient's teeth;

receiving, at the receive module, a two-dimensional un-segmented teeth image representing a current arrangement of the patient's teeth after movement of the patient's teeth;

matching, by a compare module of the analysis module, one or more teeth of the three-dimensional previously segmented teeth model to one or more corresponding teeth of the two-dimensional un-segmented teeth image, wherein the compare module is in communication with the receive module;

measuring, by the compare module, a distance between a location of a tooth in the two-dimensional teeth image and a location of a corresponding tooth in the three-dimensional previously segmented teeth model, by adjusting a position of the tooth in the three-dimensional previously segmented teeth model to the location of the tooth in the two-dimensional un-segmented teeth image; and tracking a deviation of the tooth in the two-dimensional un-segmented teeth image from an intended position of the tooth in the three-dimensional previously segmented teeth model in a stage of a patient's treatment plan if the distance between the location of the tooth in the two-dimensional un-segmented teeth image and the location of the corresponding tooth in the three-dimensional previously segmented teeth model exceed a pre-determined tolerance.

24. The computer-implemented method of claim 23, wherein the matching step comprises executing a surface matching algorithm.

25. The computer-implemented method of claim 24, wherein the surface matching algorithm comprises:

creating a grid on the three-dimensional previously segmented teeth model; and overlaying the grid onto the two-dimensional teeth image.

26. The method of claim 24, wherein the surface matching algorithm comprises:

selecting one or more sampling points from a tooth in the three-dimensional previously segmented teeth model; and identifying one or more corresponding sampling points on the two-dimensional un-segmented teeth image.

27. The computer-implemented method of claim 23, further comprising pre-processing the two-dimensional un-segmented teeth image by assigning a unique identifier to each tooth in the two-dimensional un-segmented teeth image.

28. The computer-implemented method of claim 23, wherein the matching step comprises rotating, scaling, and translating the three-dimensional teeth model to represent the two-dimensional un-segmented teeth image.

29. The computer-implemented method of claim 23, wherein the three-dimensional previously segmented teeth model represents segmented tooth data.

* * * * *